(12) United States Patent
Reipur (10) Patent No.: US 6,213,775 B1
(45) Date of Patent: Apr. 10, 2001

(54) METHOD OF FASTENING AN IMPLANT TO A BONE AND AN IMPLANT THEREFOR

(75) Inventor: John Reipur, Klampenborg (DK)

(73) Assignee: Reipur Technology A/S, Gentofte (DK)

( * ) Notice: Subject to any disclaimer, the term of this patent is extended or adjusted under 35 U.S.C. 154(b) by 0 days.

(21) Appl. No.: 09/341,223

(22) PCT Filed: Jan. 7, 1998

(86) PCT No.: PCT/DK98/00006

§ 371 Date: Aug. 13, 1999

§ 102(e) Date: Aug. 13, 1999

(87) PCT Pub. No.: WO98/30170

PCT Pub. Date: Jul. 16, 1998

(30) Foreign Application Priority Data

Jan. 7, 1997 (DK) .................................................. 0014/97

(51) Int. Cl.[7] .................................................. A61C 8/00
(52) U.S. Cl. ........................................... 433/173; 433/174
(58) Field of Search .................................. 433/172, 173, 433/174, 201.1

(56) References Cited

U.S. PATENT DOCUMENTS

| | | |
|---|---|---|
| 3,435,526 | 4/1969 | Brancato . |
| 5,004,421 | 4/1991 | Lazarof . |
| 5,439,381 | 8/1995 | Cohen . |

FOREIGN PATENT DOCUMENTS

| | | |
|---|---|---|
| WO8302555 | 8/1983 | (WO) . |
| WO9531152 | 11/1995 | (WO) . |

*Primary Examiner*—Nicholas D. Lucchesi

(57) ABSTRACT

An implant to be inserted into a bore or recess (22) of a bone, such as a jaw bone (23), comprises a radially expandable tubular member (12) which is preferably made from a helically wound string or wire, and a core member (13) to be positioned within the tubular member. The core member (13) may be moved axially in relation to the tubular member (12) so as to expand the tubular member radially, whereby the implant may be efficiently fastened. The core member (13) may be screwed into the outer tubular member (12) or into an anchoring member (11) arranged at the inner end of the recess (22). The implant is relatively easy to remove if such removal should become necessary by radially contracting the tubular member (12).

38 Claims, 6 Drawing Sheets

METHOD OF FASTENING AN IMPLANT TO A BONE AND AN IMPLANT THEREFOR

This application is the national phase under 35 U.S.C. §371 of PCT International Application No. PCT/DK98/00006 which has an International filing date of Jan. 7, 1998 which designated the United States of America.

The present invention relates to a method of fastening an implant to a bone.

It is known to insert an implant in a bore or recess formed in a jawbone so that an artificial tooth may be mounted at the outer end of the implant. The outer surface of the implant may have grooves or channels formed therein so that the implant is efficiently fastened to the jawbone when bone tissue eventually grows into intimate contact with the outer surface of the implant. Infection may cause destruction of bone tissue in contact with the implant to such an extent that the implant has to be removed from the jawbone. Such removal of the implant and reinsertion of a new implant is a complicated operation involving removal of bone tissue and enlargement the bore or recess in which the new implant is inserted.

It is also known to insert an implant into the medullary cavity of a bone. Such implant may for example include part of an artificial hipjoint. The insertion of known implants in medullary cavities normally involves the use of so-called bone cement. Bone cement may decompose so that the implant gets loose. Consequently, the patient has to undergo a new surgical operation.

The present invention provides a method allowing an improved and more efficient fastening of an implant to a bone.

Thus, the present invention provides a method of fastening an implant to a bone, said implant comprising a core member and a radially expandable outer tubular member, which includes a helically wound elongated member, said method comprising forming a bore or recess in the bone, arranging the radially expandable tubular member in said bore or recess, positioning the core member so as to at least partly extend into the expandable tubular member, releasably fastening the core member in this position in relation to the tubular member, and allowing bone tissue to grow into intimate contact with the outer surface of the tubular member.

When the tubular member has been inserted into the bore or recess formed in the bone the tubular member may be radially expanded, for example by means of the core member which is inserted into and fastened to the tubular member. This means that the outer surface of the tubular member may be moved into engagement with the inner surface of the bore or recess formed in the bone, whereby a good initial fastening of the implant to the bone may be obtained. Furthermore, as explained below the tubular member may later rather easily be removed from the bone, if necessary.

The core member may be moved into and releasably fastened to the tubular member in any suitable manner. As an example, outer thread-like formations formed on the core member may be engaged with inner tread-like formations formed in the tubular member.

An anchoring member may be arranged at the inner end at the bore or recess in the bone and may be releasably connected to an adjacent end of the tubular member and/or the core member. Such anchoring member, which is arranged at the inner end of the recess or bore may usually remain in the recess or bore in case it is necessary to remove and replace the tubular member and the core member. A new tubular member and core member may then be inserted in the recess and efficiently fixed when they are fastened to the already fixed anchoring member. The anchoring member may have any size and shape. Usually, it is preferred that the maximum radial dimension of the anchoring member exceeds that of the adjacent end of the tubular member.

In a preferred embodiment an outer thread-like formation formed on the core member at the inner end thereof is engaged with an inner thread-like formation at an inner surface part of the anchoring member. The core member may then be moved axially in relation to the tubular member by screwing the core member into the anchoring member.

The helically wound elongated member forming part of the tubular member is preferably a string or wire. The windings of the helically wound elongated member may be in mutual abutting engagement. In this case the helically wound elongated member may form a tubular member having a substantially closed peripheral wall. Alternatively, adjacent windings of the helically wound elongated member may be slightly spaced in the axial direction of the tubular member. In order to obtain an unbroken peripheral wall of the tubular member adjacent windings of the helically wound elongated member may be interconnected by preferably thin, tearable wall parts.

When the implant is mounted in the bore or recess of the bone the tubular member may be inserted first and the core member may thereafter be inserted into the tubular member. Preferably, however, the core member is positioned within the tubular member prior to arranging the tubular member in the bore or recess. The core member may thereafter be moved axially in relation to the tubular member.

The outer surface of the tubular member may have any suitable shape and may, for example, be generally cylindrical. However, in order to facilitate a possible later removal of the implant the outer surface of the tubular member may be tapered toward the inner end of the bore or recess formed in the bone. As an example, the tapered outer surface of the tubular member may be frustoconical.

The outer surface of the core member and the inner surface of the tubular member cooperating therewith are preferably such that the tubular member arranged in the bore or recess formed in the bone is expanded radially by moving the core member axially inwardly into the expandable tubular member. As an example, the core member may comprise an outer, generally conical surface of the core member cooperating with a corresponding inner, generally conical surface of the tubular member.

The implant comprising an anchoring member, an outer tubular member, and an inner core member preferably forms a unit which is inserted into the bore or recess of the bone. Therefore, the anchoring member is preferably releasably connected to the tubular member and/or the core member prior to inserting said members into the bore or recess in the bone.

The bore or recess may, for example, be formed in a jawbone, and an artificial tooth may be fastened to the outer end portion of the core member. Alternatively, the bore or recess may at least partly be formed by the medullary cavity of a bone. In the latter case part of an artificial hipjoint may be connected to the core member. When the implant has been inserted in the medullary cavity of a bone the expandable tubular member may be expanded as described above, whereby the implant may be effectively fastened to the bone to such an extent that the use of bone cement may become unnecessary. If an implant which have been mounted by the method according to the invention should get loose it would be possible later to further fastened the implant by tightening the thread connection between the core member and the tubular member or the anchoring member so as to further expand the tubular member into intimate contact with the inner walls of the medullary cavity. Such tightening would involve only a minor surgical operation.

The tubular member, the anchoring member, and/or the core member should be made from physiologically tolerable materials which may be accepted by the human or animal body in which it is to be used. Such materials include titanium, plastic, and any other material conventionally used for implants.

If, for some reason, the implant has to be removed from a bone in which it has been embedded for a shorter or longer period of time the core member is first released from the tubular member and the tubular member is subsequently removed from the bore or recess in the bone. Bone tissue may have grown into depressions or grooves formed in the outer surface of the tubular member, whereby a strong adherence has been established between the tissue and the tubular member. However, because the tubular member is at least partly formed by a helically wound elongated member the tubular member may be removed by pulling the outer end of the elongated member so as to unwind or straightened the elongated member. Thereby the removal of the tubular member is substantially facilitated.

Alternatively, the tubular member may be removed by arranging a tool along the longitudinal axis of the tubular member, fastening a free end of the elongated member to the tool and rotating the tool about its longitudinal axis so as to reduce the outer diameter of the tubular member. When in this manner the tubular member has been removed from its contact with the bone tissue it may easily be removed from the bore or recess.

The present invention also provides an implant to be inserted in a bore or recess formed in a bone, said implant comprising a radially expandable tubular member, a core member to be positioned within the tubular member so as to at least partly extend into the expandable tubular member, means for axially moving the core member in relation to the outer tubular member, and means for releasably retaining the core member in a selected position in relation to the tubular member. The tubular member and the core member may then be provided with cooperating inner and outer surfaces formed so as to cause a radial expansion of the tubular member when the core member is moved axially into the tubular member so as to efficiently fasten the implant to the bone. The radially expandable tubular member may comprise or be formed by a helically wound elongated member, such as a string or wire. Adjacent windings of the helically wound elongated member may be in mutual abutting engagement or may be slightly axially spaced. In either case adjacent windings may be interconnected by wall parts which preferably are thin and tearable so as to allow removal of the tubular member by pulling the outer end of the elongated member so as to unwind and straighten it.

The moving and retaining means may comprise thread-like formations which are formed on the core member and adapted to engage with inner tread-like formations formed in the tubular member. The inner thread-like formations of the tubular member may be formed by the helically wound elongated member which may also form outer thread-like formations on the tubular member. As mentioned above, the implant may further comprise an anchoring member and means, such as thread means, may be provided for releasably connecting the anchoring member to the inner end of the tubular member and/or the core member.

It should be understood that the outer tubular member need not necessarily be made from a helically wound elongated member, but could have any shape allowing a certain radial expansible thereof. It is also envisaged that it is not strictly necessary that the tubular member is radially expansive. Thus, when the implant comprises an anchoring member as described above the tubular member could have an inwardly tapered outer surface which could be moved into contact with the inner wall of the bore or recess when the tubular member is connected to and moved inwardly in relation to the already fixed anchoring member.

The invention will now be further described with reference to the drawings, wherein.

Figure 1:
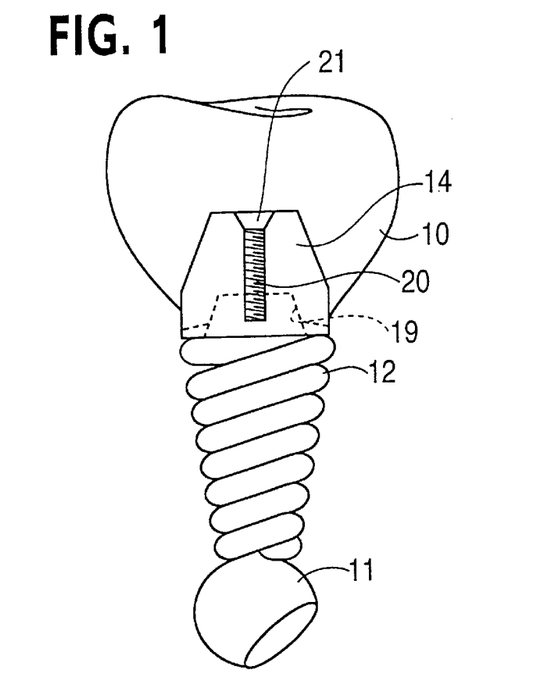
FIG. 1 is a side view of a first embodiment of the implant according to the invention.
Figure 2:
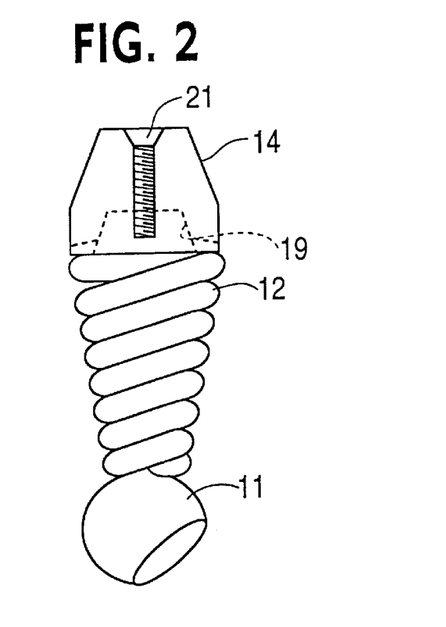
FIGS. 2–4 illustrate the various parts of the implant.
Figure 3:
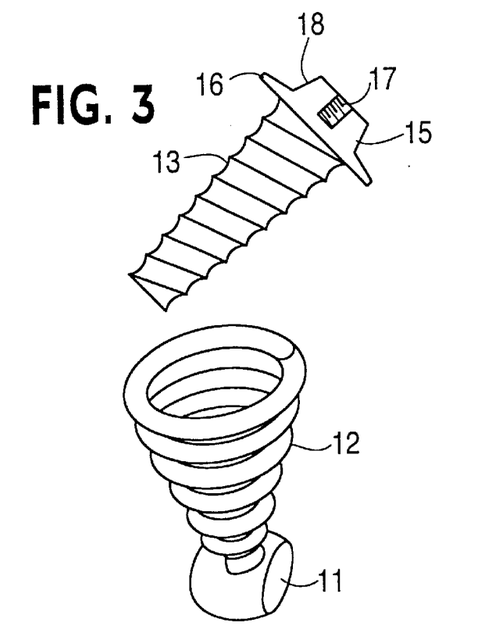
Figure 4:
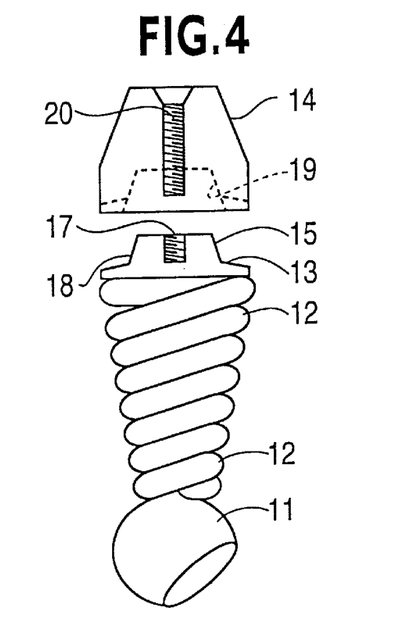

FIG. 1 shows an implant for fastening an artificial tooth 10 and to be mounted in a bore or recess formed in a jawbone, for example a cavity from which the root of a natural tooth has been removed. The implant comprises and inner anchoring member 11, a tubular member 12, a core member 13, and an abutment member 14 to which the artificial crown of a tooth 10 may be fastened.

In the embodiment shown the anchoring member 11 has the shape of a spherical segment and is releasably fastened to the inner end of the tubular member 12. The tubular member 12 is formed by a helically wound wire or string and is tapered towards the anchoring member 11. The windings of the wire or string define inner and outer threads on the tubular member.

The core member 13 has a tapered conical shape which is complementary to the inner surface of the tubular member 12. Thus the outer surface of the core member 13 has thread-like formations which may engage with the inner threads of the tubular member 12. The core member 13 also has a head 15 with a radially extended collar 16 and an axially extending threaded bore 17. The head 15 of the core member 13 also defines an outer frustoconical surface 18 which is received in a recess 19 formed in the abutment member 14 having a frustoconical surface which is complementary to the surface 18. The abutment member 14 also has a through axial bore 20 for receiving a fastening screw 21 which may engage with the threaded bore 17 of the core member head 15 so as to fasten the abutment member 14 to the core member 13.

The implant comprising the anchoring member 11, the tubular member 12, and the core member 13 may be inserted in a recess or bore formed in a jawbone where an artificial tooth should be mounted. When the implant has been inserted in the jawbone the tubular member 12 may be expanded radially by screwing the core member 13 into the tubular member whereby the outer surface of the tubular member may be moved into tight engagement with the outer peripheral wall of the bore or recess formed in the jawbone. The abutment member 14 may then be fastened to the core member 13 by means of the screw 21, and finally, the artificial tooth crown 10 may be fastened to the abutment member 14 in a conventional manner.

Figure 5:
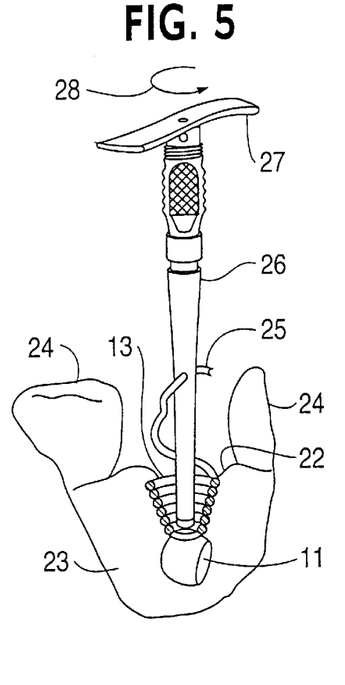
FIGS. 5 and 6 illustrate how the outer tubular part of the implant may be removed from a jawbone.
Figure 6:
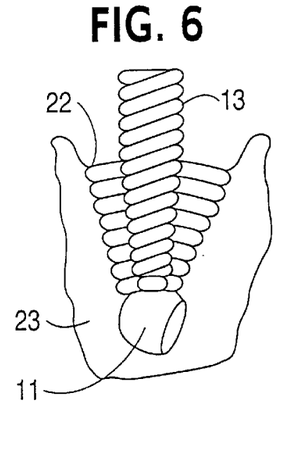
Figure 7:
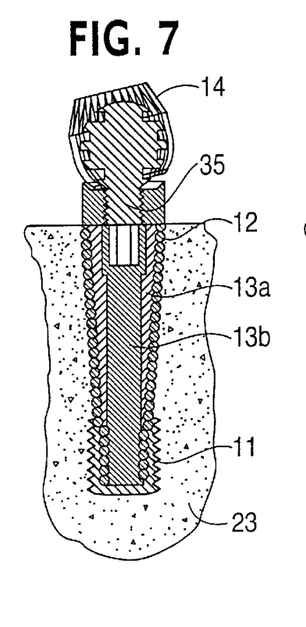
FIG. 7 is a sectional view illustrating a second embodiment of the implant according to the invention mounted in a jawbone.

FIGS. 5 and 6 illustrate how an implant of the type shown in FIGS. 1–4 may be removed from a recess 22 in a jawbone 23 in which it has been mounted for a certain period of time so that bone tissue has grown into intimate contact with the outer surface of the tubular member 13. As shown in FIG. 5, the recess 22 in the jawbone may be located between a pair of adjacent natural teeth 24. When the abutment member 14 has been removed by unscrewing the fastening screw 21 the core member 13 may be screwed out of the tubular member 13. Thereafter the outer free end 25 of the wire or string forming the tubular member 13 may be fastened to a rod-shaped tool 26 which has been inserted axially into the recess 22 and which has a handle 27 at its outer end. By rotating the tool 26 about its axis in a direction indicated by an arrow 28 the tubular member 12 may be contacted radially as illustrated in FIG. 6 and thereby loosened from the bone tissue forming the peripheral wall of the recess 22. Now, the tubular member 13 may be released from the anchoring member 11 and removed. The anchoring member 11 may remain in its position and may be used when a new implant is inserted into the recess 22.

FIGS. 7–19 illustrate further embodiments of implants of the type adapted to be mounted in a jawbone in order to fasten an artificial tooth crown to the jawbone 23, and in the following description parts corresponding to the parts shown in FIGS. 1–6 will be designated the same reference numerals.

Figure 8:
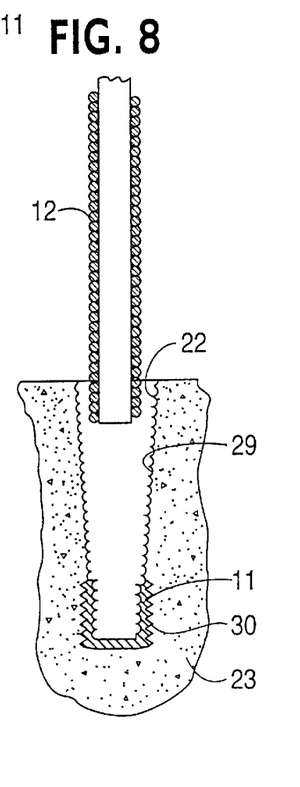
FIGS. 8–11 are sectional views illustrating various steps in mounting the implant in the jawbone.
Figure 9:
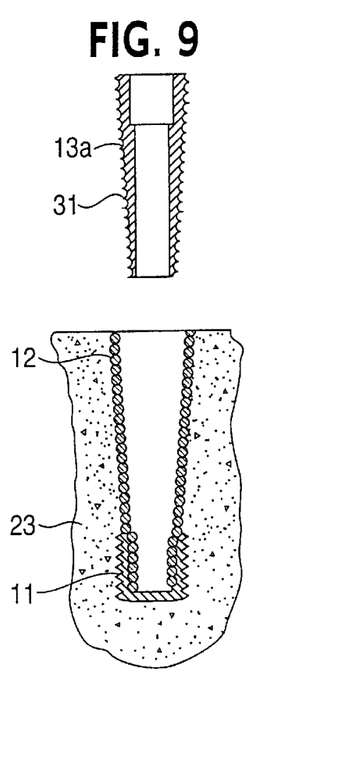
Figure 10:
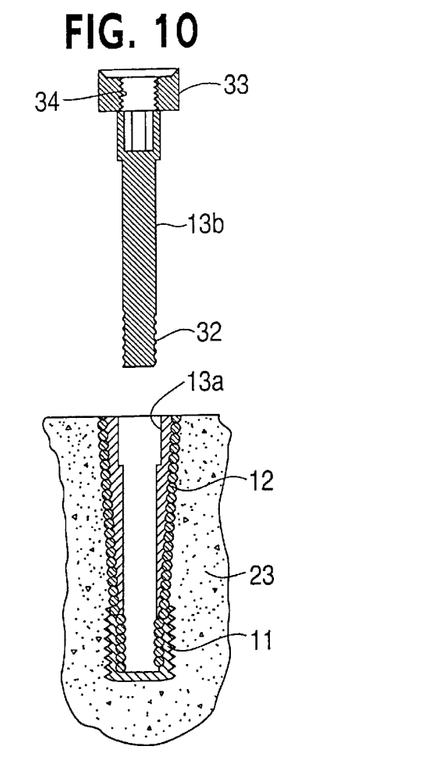
Figure 11:
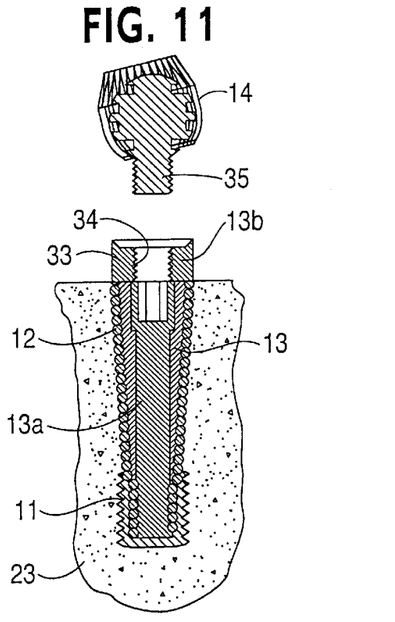
Figure 12:
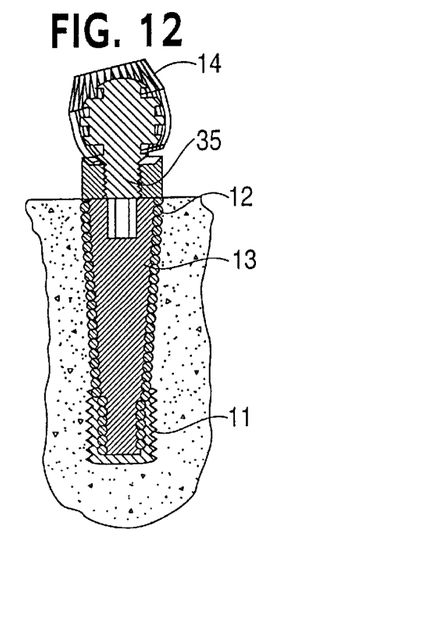
FIG. 12 is a sectional view of a third embodiment of the implant according to the invention mounted in a jawbone.
Figure 13:
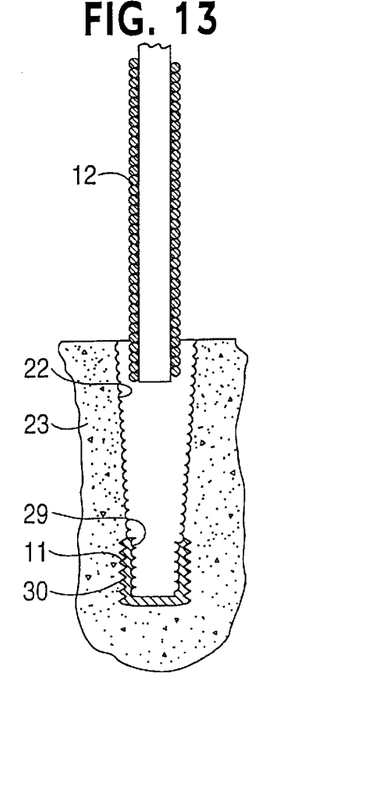
FIGS. 13–15 are sectional views illustrating various steps of mounting the implant.
Figure 14:
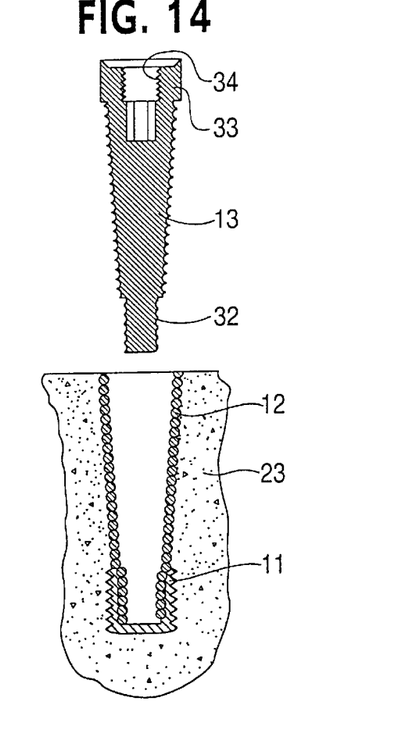
Figure 15:
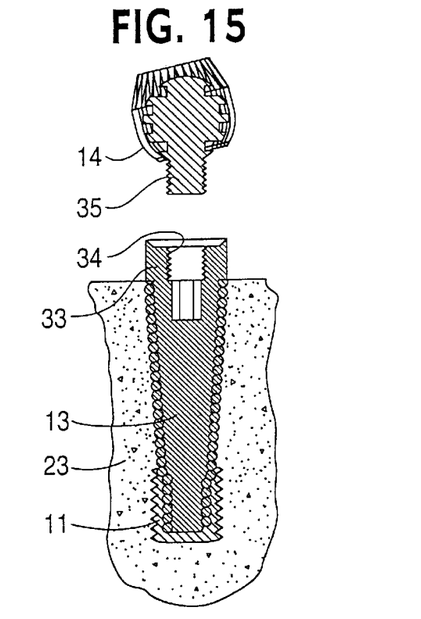
Figure 16:
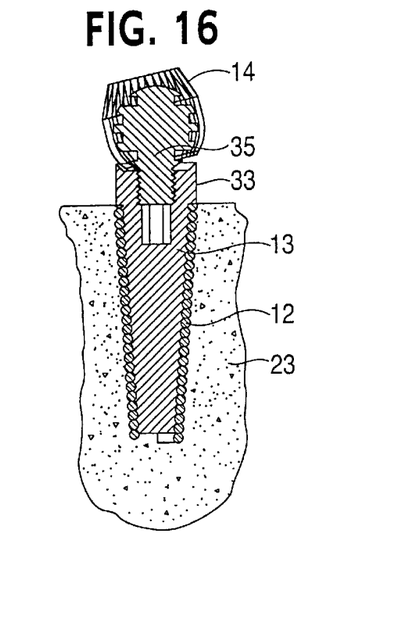
FIG. 16 is a sectional view of a fourth embodiment of the implant according to the invention.
Figure 17:
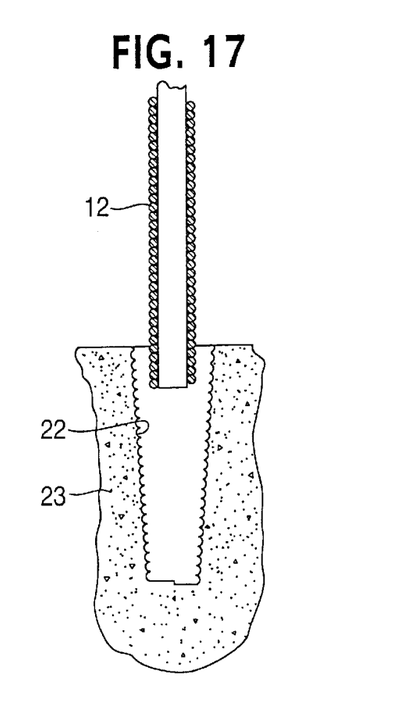
FIGS. 17–19 are sectional views illustrating the various steps of mounting the implant in a jawbone.
Figure 18:
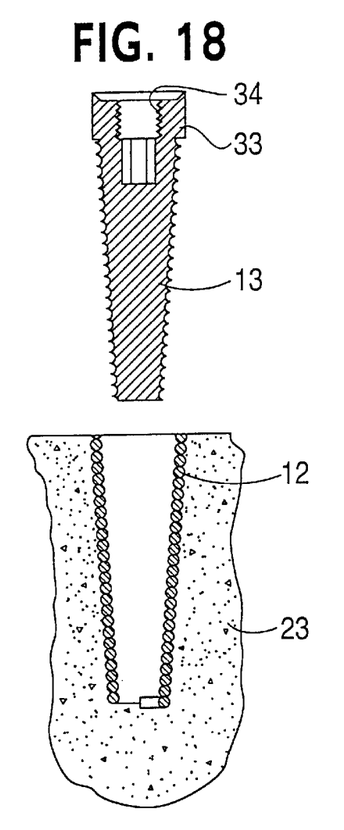
Figure 19:
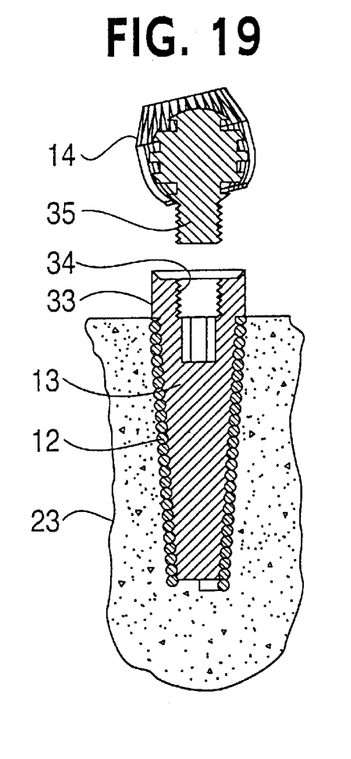

In the embodiment shown in FIGS. 7–11 the anchoring member 11 which is mounted at the inner end of the conical or tapered recess or bore 12 has a substantially cylindrical peripheral wall. The peripheral wall of the anchoring member 11 is provided with inner and outer threads 29 and 30, respectively. As shown in FIG. 8 the tubular member 12 is inserted into the recess 22 in a radially contracted, substantially cylindrical condition, and the inner end of the tubular member 12 is positioned within the anchoring member 11. When a tubular member 12, which is formed by a helically wound wire or string, is released the resiliency of the tubular member causes a radial extension of the tubular member so as to move the outer surface thereof into close contact with the inner threads 29 of the anchoring member 11 and the inner walls of the recess 22, respectively, as illustrated in FIG. 9. The core member 13 comprises an outer tubular core element 13a having outer threads and an inner core element 13b fittin into the tubular element 13a. As shown in FIG. 10, the outer tubular element 13a may be screwed into engagement with the inner surface of the tubular member 12, whereby the tubular member may be further radially extended, and the inner core element 13 may thereafter be inserted into the bore of the tubular element 13a, and the inner free end of the element 13b is provided with outer threads 32 which may engage with the inner thread-like formations formed by the inner end of the tubular member 12 which is located within the anchoring member 11. An enlarged head 33 at the outer end of the inner core element 13b has an axial threaded bore 34 formed therein, and the abutment member, which is adapted to receive an artificial tooth crown (not shown) has a threaded neck 35 which may be screwed into the threaded bore 34 whereby the abutment member 14 is fastened to the inner core element 13b.

FIGS. 12–15 illustrate a modification of the embodiment shown in FIGS. 7–11. In the embodiment shown in FIGS. 12–15 the core member 13 is a single unitary part, which is not divided into two separate elements as shown in FIGS. 7–11. Otherwise the two embodiments are alike.

The embodiment of the implant shown in FIGS. 16–19 does not comprise an anchoring member and, consequently, the core member 13 does not have a cylindrical inner end portion with threads 32 to cooperate with the anchoring member. In all other respects the embodiment shown in FIGS. 16–19 substantially corresponds to that shown in FIGS. 12–15.

Figure 20:
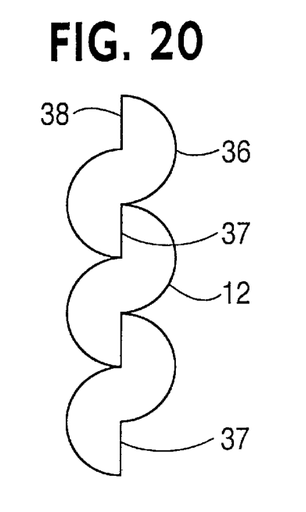
FIGS. 20 and 21 are fragmentary sectional views showing different cross-sectional shapes of the elongated member and how adjacent windings are interengaging.
Figure 21:
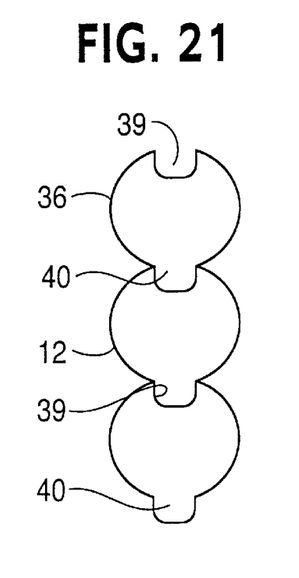

Adjacent windings of the helically wound string or wire from which the tubular member 12 is made is preferably in close mutual contact in the mounted condition of the implant in order to prevent bone tissue from growing into the inner space of the tubular member. FIGS. 20 and 21 illustrate different cross-sectional shapes of the string or wire allowing such close contact. The helically wound wire or string 36 shown in FIG. 20 defines inner and outer surface parts 37 and 38, respectively, which may be in mutual abutting contact whether or not the tubular member 12 is more or less radially expanded. In the embodiment shown in FIG. 21 the wire or string has a channel 39 and a diametrically oppositely extending projection or ridge 40 such that the ridge 40 may fit into the channel 39 of an adjacent winding of the wire or string 36.

Figure 22:
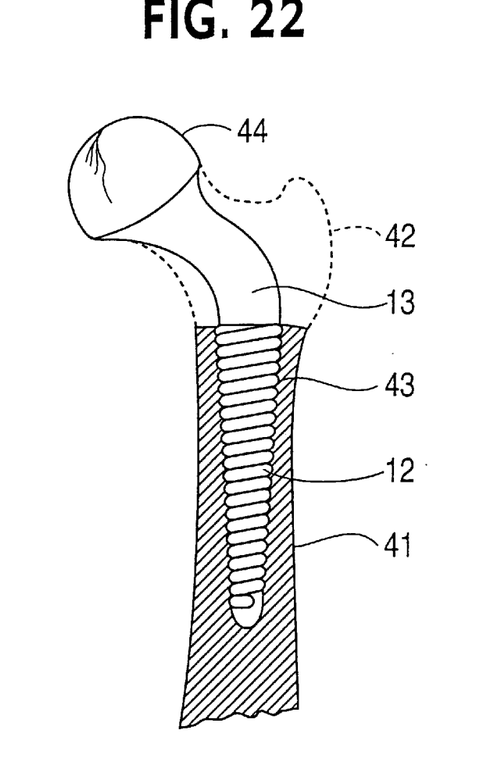
FIG. 22 is a cross-sectional view showing an implant according to the invention mounted in the medullary cavity of a bone.

FIG. 22 shows a longitudinal section of a thighbone 41 from which an end portion 42 has been cut off so as to expose the medullary cavity of the bone. An implant 43, which may be of any of the embodiments described above, is inserted into and fixed in the medullary cavity by expanding the outer tubular member 12 in a manner previously described. The outer end of the core member 13 of the implant may be formed as a hip joint part 44 or such artificial hip joint part may be fastened to the core member 13 in any suitable manner. A complementary artificial hip joint part (not shown) may in a similar manner be mounted to the hipbone whereby a natural hip joint may be replaced by an artificial one.

Figure 23:
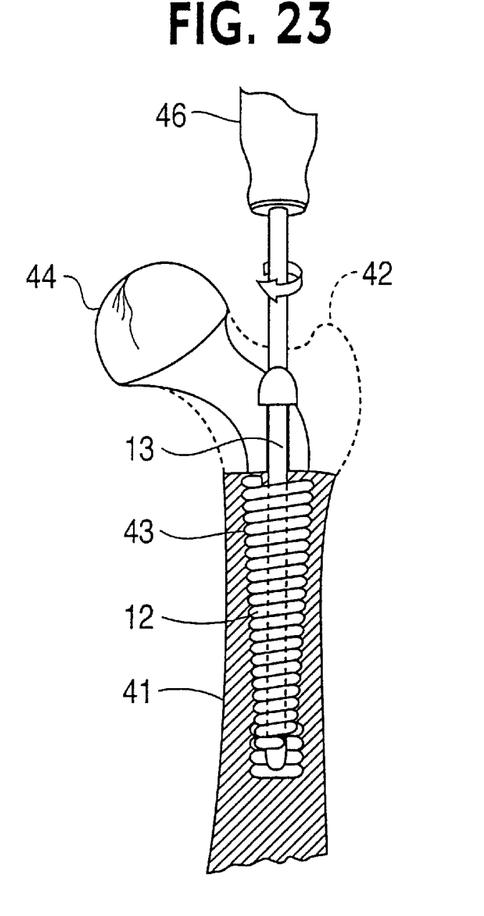
FIG. 23 illustrates how the implant shown in FIG. 22 may be fastened.

As illustrated in FIG. 23 the helically wound tubular member 12 which is mounted in the medullary cavity of the thighbone may be further expanded gradually and fastened or contracted radially so that it may be removed. For this purpose the core member 13 may comprise a rotatable, axially extending actuating member 45, which may be rotated by a suitable tool such as a screw driver.

It should be understood that various embodiments and modifications of the embodiments shown could be made without departing from the scope of the present invention. Thus, features and parts disclosed in the various drawings may be combined or interchanged.

What is claimed is:

1. A method of fastening an implant to a bone, said implant comprising a core member and a radially expandable outer tubular member, which includes a helically wound elongated member defining an outer peripheral surface of the tubular member, said method comprising
    forming an inwardly tapering bore or recess in the bone,
    arranging the radially expandable tubular member in said bore or recess,
    moving the core member into the tubular member so as to expand the tubular member radially,
    releasably fastening the core member in relation to the tubular member in a position in which the tubular member is in contact with walls defining the bore or recess, and allowing bone tissue to grow into intimate contact with the outer surface of the tubular member.

2. A method according to claim 1, wherein outer thread-like formations formed on the core member are engaged with inner thread-like formations formed in the tubular member.

3. A method according to claim 1, further comprising arranging an anchoring member at the inner end of the bore or recess in the bone and releasably connecting the anchoring member to an adjacent end of the tubular member and/or the core member.

4. A method according to claim 3, wherein the maximum radial dimension of the anchoring member exceeds that of the adjacent end of the tubular member.

5. A method according to claim 3, wherein an outer thread-like formation formed on the core member at the inner end thereof is engaged with an inner thread-like formation at an inner surface part of the anchoring member.

6. A method according to claim 3, wherein the anchoring member is releasably connected to the tubular member prior to inserting said members into the bore or recess in the bone.

7. A method according to claim 1, wherein the elongated member is a string or wire.

8. A method according to claim 1–7, wherein the windings of the helically wound elongated member are in mutual abutting engagement.

9. A method according to claim 1–8, wherein adjacent windings of the helically wound elongated member are interconnected by tearable wall parts.

10. A method according to claim 1–9, wherein the core member is positioned in the tubular member prior to arranging the tubular member within the bore or recess.

11. A method according to claim 1–10, wherein the outer surface of the tubular member is frustoconical.

12. A method according to claim 1, wherein the bore or recess is formed in a jawbone, and an artificial tooth is fastened to the outer end portion of the core member.

13. A method according to claim 1, wherein the bore or recess is at least partly formed by the medullary cavity of a bone.

14. A method according to claim 13, wherein part of an artificial hip joint is connected to the core member.

15. A method according to claim 1, wherein the tubular member, the anchoring member, and the core member are made from a physiologically tolerable material.

16. A method according to claim 1, further comprising releasing the core member from the tubular member and subsequently removing the tubular member from the bore or recess.

17. A method according to claim 16, wherein the tubular member is removed by pulling the outer end of the elongated member so as to unwind or straighten the elongated member.

18. A method according to claim 17, wherein the tubular member is removed by arranging a tool along the longitudinal axis of the tubular member, fastening the outer end of the elongated member to the tool and rotating the tool about its longitudinal axis so as to reduce the outer diameter of the tubular member.

19. A method according to claim 1, wherein the anchoring member is releasably connected to the core member prior to inserting said members into the bore or recess in the bone.

20. An implant to be positioned in a bore or recess formed in a bone, said implanting comprising:
an outer radially expandable tubular member which includes a helically wound, elongated member defining an outer peripheral surface of the tubular member,
a core member to be positioned within the outer tubular member so as to at least partly extend into the expandable tubular member from an outer end thereof,
means for axially moving the core member in relation to the outer tubular member so as to expand the tubular body radially, and
means for releasably retaining the core member in a selected position in relation to the tubular member, in its expanded condition the outer tubular member being tapered towards an inner end opposite to said outer end.

21. An implant according to claim 20, wherein outer thread-like formations formed on the core member are adapted to engage with inner thread-like formations formed in the tubular member.

22. An implant according to claim 20 further comprising an anchoring member, and means for releasably connecting the anchoring member to the inner end of the tubular member.

23. An implant according to claim 22, wherein the minimum radial dimension of the anchoring member exceeds that of the inner end of the tubular member.

24. An implant according to claim 22 or 23, wherein outer thread-like formations formed on the core member are adapted to engage with inner thread-like formations at an inner surface of the anchoring member.

25. An implant according to claim 22, wherein the anchoring member is a nut-like member.

26. An implant according to claim 20, wherein the elongated member is a string or wire.

27. An implant according to claim 20, wherein the windings of the helically wound elongated member are in mutual abutting engagement.

28. An implant according to claim 20, wherein adjacent windings of the helically wound elongated member are interconnected by tearable wall parts.

29. An implant according to claim 20, wherein the outer surface of the tubular member is tapered toward the inner end when the tubular member is in its unexpanded condition.

30. An implant according to claim 29, wherein the outer surface of the tubular member has a conical or frustoconical shape.

31. An implant according to claim 20, wherein the implant is adapted to be inserted in a bore or recess formed in a jawbone, the outer free end portion of the core member having means for fastening an artificial tooth thereto.

32. An implant according to claim 20, wherein the implant is adapted to be inserted into a bore or recess at least partly being formed by the medullary cavity of a bone.

33. An implant according to claim 32, wherein the implant comprises part of an artificial hip joint connected to or forming part of the core member.

34. An implant according to claim 20, wherein the tubular member, the anchoring member, and the core member comprise a physiologically tolerable material.

35. An implant according to claim 34, wherein the tubular member is made from titanium wire.

36. An implant according to claim 20, wherein the core member has a shape tapering toward an inner end thereof.

37. An implant according to claim 36, wherein the tubular member has a substantially cylindrical shape in its unexpanded condition.

38. An implant according to claim 20, further comprising an anchoring member and means for releasably connecting the anchoring member to the inner end of the core member.

* * * * *